(12) United States Patent
Kiyotoh et al.

(10) Patent No.: US 10,722,570 B2
(45) Date of Patent: Jul. 28, 2020

(54) DRIED INFLUENZA VACCINE PREPARATION AND METHOD FOR PRODUCING DRIED INFLUENZA VACCINE PREPARATION

(71) Applicant: NITTO DENKO CORPORATION, Osaka (JP)

(72) Inventors: Eiji Kiyotoh, Osaka (JP); Mitsuhiko Hori, Osaka (JP); Daisuke Asari, Osaka (JP); Katsuyuki Okubo, Osaka (JP); Takuya Shishido, Osaka (JP); Masahiro Fukasaka, Osaka (JP); Kyohei Matsushita, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 15/777,441

(22) PCT Filed: Nov. 28, 2016

(86) PCT No.: PCT/JP2016/085161
§ 371 (c)(1),
(2) Date: May 18, 2018

(87) PCT Pub. No.: WO2017/090769
PCT Pub. Date: Jun. 1, 2017

(65) Prior Publication Data
US 2018/0326042 A1 Nov. 15, 2018

(30) Foreign Application Priority Data

Nov. 27, 2015 (JP) .................. 2015-232448

(51) Int. Cl.
| | | |
|---|---|---|
| A61K 39/00 | (2006.01) |
| C07K 14/00 | (2006.01) |
| C12N 9/90 | (2006.01) |
| A61K 38/00 | (2006.01) |
| A61K 39/108 | (2006.01) |
| A61K 39/145 | (2006.01) |
| A61K 47/26 | (2006.01) |
| A61K 9/19 | (2006.01) |
| A61K 47/18 | (2017.01) |
| A61P 31/16 | (2006.01) |

(52) U.S. Cl.
CPC .............. *A61K 39/145* (2013.01); *A61K 9/19* (2013.01); *A61K 39/00* (2013.01); *A61K 47/18* (2013.01); *A61K 47/183* (2013.01); *A61K 47/26* (2013.01); *A61P 31/16* (2018.01); *A61K 2039/5252* (2013.01); *A61K 2039/55511* (2013.01)

(58) Field of Classification Search
CPC ................ A61K 2300/00; A61K 39/00; A61K 2039/505; A61K 31/56; C12N 15/8245
See application file for complete search history.

(56) References Cited

U.S. PATENT DOCUMENTS

| | | | |
|---|---|---|---|
| 2003/0219475 A1* | 11/2003 | Truong-Le | A61K 9/0019 424/450 |
| 2004/0013695 A1* | 1/2004 | Vande-Velde | A61K 9/0053 424/400 |
| 2009/0232894 A1 | 9/2009 | Chouvenc et al. | |
| 2010/0104595 A1 | 4/2010 | Yamashita | |
| 2016/0220483 A1* | 8/2016 | Mistilis | A61K 9/0021 |

FOREIGN PATENT DOCUMENTS

| | | |
|---|---|---|
| CN | 101524537 A | 9/2009 |
| EP | 3 381 467 A1 | 10/2018 |
| JP | 2004-506020 A | 2/2004 |
| JP | 2005-538939 A | 12/2005 |
| JP | 2011-514899 A | 5/2011 |
| JP | 5388842 B2 | 10/2013 |
| WO | 02/13858 A1 | 2/2002 |
| WO | 2002/101412 A2 | 12/2002 |
| WO | 03/087327 A2 | 10/2003 |
| WO | 2004/058156 A2 | 7/2004 |
| WO | WO 2007/038926 A1 | 4/2007 |
| WO | WO2012158978 * | 11/2012 |
| WO | 2015/034924 A1 | 3/2015 |

OTHER PUBLICATIONS

International Search Report from Patent Application No. PCT/JP2016/085161, dated Jan. 17, 2017.
International Preliminary Report on Patentability from Patent Application No. PCT/JP2016/085161, dated May 29, 2018.
EESR for EP App. No. 16 86 8712.7 dated May 6, 2019.

* cited by examiner

*Primary Examiner* — Barry A Chestnut
(74) *Attorney, Agent, or Firm* — Greenblum & Bersntein, P.L.C.

(57) ABSTRACT

The present invention provides a dried influenza vaccine preparation in which the activity of an influenza vaccine can be stably maintained even if the preparation is stored without strict temperature control and which can be stably supplied. The present invention also provides a method for producing the dried influenza vaccine preparation. Provided is a dried influenza vaccine preparation including: an influenza vaccine antigen; a disaccharide; and an amino acid.

5 Claims, No Drawings

DRIED INFLUENZA VACCINE PREPARATION AND METHOD FOR PRODUCING DRIED INFLUENZA VACCINE PREPARATION

TECHNICAL FIELD

The present invention relates to a dried preparation containing an influenza vaccine. More specifically, the present invention relates to a dried influenza vaccine preparation in which the activity of an influenza vaccine can be stably maintained even if the preparation is stored without strict temperature control and which can be stably supplied. The present invention also relates to a method for producing the dried influenza vaccine preparation.

BACKGROUND ART

Influenza is a type of acute infection caused by an influenza virus. The incubation period from infection with the influenza virus to onset of influenza is usually one to two days. The onset is accompanied by the following symptoms, for example: a fever of 38 degrees or higher, systemic symptoms (such as general malaise, headache, joint pain, and muscle pain), sore throat, cough, and nasal discharge. In general, recovery takes one week or less. Influenza may lead to complications such as pneumonia and bronchitis, which may become severe and result in death, in the case of onset of influenza in people such as elderly people, infants, pregnant women, patients with chronic respiratory disease, patients with chronic cardiovascular disease, diabetic patients, and chronic renal failure patients. In addition, influenza intensively occurs in epidemics in a short period of time, and thus sometimes affects the society and causes an economic loss.

Administration of influenza vaccine is the most effective method of preventing influenza from becoming severe. An influenza vaccine preparation is usually a liquid preparation used as an injectable drug or nasal preparation.

For distribution of a liquid preparation of influenza vaccine, temperature control (so-called a cold chain) is required throughout the entire process of distribution and storage in order to prevent deactivaton of the influenza vaccine. Although the epidemic season is different depending on the region, influenza is pandemic, and it is difficult to distribute the preparation while maintaining the activity of the influenza vaccine antigen in the countries and regions where the temperature control is difficult.

Currently available influenza vaccines are roughly divided into live attenuated influenza vaccines and inactivated influenza vaccines. Further, inactivated influenza vaccines are classified into the following three groups: (1) whole virus inactivated with formalin or the like; (2) split vaccine obtained by disrupting virus particles with an organic solvent or a surfactant and solubilizing lipid envelopes; and (3) subunit vaccine obtained by purifying hemagglutinin (HA) and neuraminidase (NA). Among these, two types of vaccines, i.e., split vaccines and subunit vaccines, are currently available as commercial influenza vaccines. Both of these vaccines are usually prepared by disrupting virus particles with an organic solvent or a surfactant and isolating or purifying viral proteins depending on the type.

However, while influenza virus particles have a high sterol content and are usually stable, problems such as a time-dependent decrease in the titer occur during a storage period in the case where the vaccine is obtained by disrupting virus particles, removing lipid substances from the virus particles, and isolating or purifying viral proteins. As described above, since the split vaccine and the subunit vaccine are not necessarily stable, temperature control is required throughout the entire process of distribution and storage in order to maintain the activity of the influenza vaccine antigen.

As a method of overcoming the above-described drawback of the liquid preparation of influenza vaccine, an attempt has been made to produce a preparation in dry form.

For example, Patent Literature 1 discloses production of particles by spray-drying an influenza virus together with a thickener. Patent Literature 2 discloses production of a powder by spray-drying an antigen together with various additives. Patent Literature 3 discloses a pharmaceutical composition in which an attenuated influenza virus as a live influenza vaccine is stabilized by lyophilizing a vaccine solution containing sucrose as a stabilizer, dextran as a bonding agent, and xanthan gum as an excipient. Patent Literature 4 discloses a pharmaceutical composition in which an influenza HA vaccine is stabilized by lyophilizing a vaccine solution containing a hydrophobic amino acid (phenylalanine, valine, leucine, and isoleucine) and arginine hydrochloride as stabilizers.

A seasonal influenza HA vaccine is a vaccine reformulated annually for specific strains, and a mixed type vaccine such as a trivalent vaccine (two strains of type A and one strain of type B) or a tetravalent vaccine (two strains of type A and two strains of type B) is a mainstream vaccine. However, since the amino acid sequence or conformation is different according to the viral type, it is difficult to stably store a pharmaceutical composition containing plural influenza HA vaccines by conventional vaccine formulation techniques.

CITATION LIST

Patent Literature

Patent Literature 1: WO 2004/058156
Patent Literature 2: WO 2002/101412
Patent Literature 3: WO 2002/013858
Patent Literature 4: JP 5388842 B

SUMMARY OF INVENTION

Technical Problem

In view of the above-described situation, the present invention aims to provide a dried influenza vaccine preparation in which the activity of an influenza vaccine can be stably maintained even if the preparation is stored without strict temperature control and which can be stably supplied.

The present invention also aims to provide a method for producing a dried influenza vaccine preparation in which the activity of a contained influenza vaccine antigen is not lowered during the production process of the dried influenza vaccine preparation.

Solution to Problem

In order to solve the above-described problem, the present inventors conducted intensive examinations to find that, in a dried influenza vaccine preparation containing, among various additives, a disaccharide and an amino acid, the activity of the influenza vaccine can be stably maintained even if the preparation is stored without strict temperature control, unlike the case of conventional liquid preparations.

In addition, the dried influenza vaccine preparation is prepared in such a manner that the activity of the influenza vaccine is stabilized by a disaccharide and an amino acid which can be supplied at low cost. Thus, such a dried influenza vaccine preparation can also be stably supplied.

In other words, the present invention provides a dried influenza vaccine preparation including: an influenza vaccine antigen; a disaccharide, and an amino acid.

The disaccharide is preferably at least one selected from the group consisting of trehalose, isomalt, sucrose, maltose, melibiose, palatinose, and lactulose.

The amino acid is preferably at least one selected from the group consisting of arginine, lysine, proline, threonine, ornithine, alanine, cysteine, phenylalanine, glycine, hydroxyproline, and salts of these.

The influenza virus antigen is preferably an inactivated antigen. The inactivated antigen is preferably a split vaccine antigen or a subunit vaccine antigen. In particular, the inactivated antigen is preferably a split vaccine antigen.

The present invention also relates to a method for producing a dried influenza vaccine preparation including: drying an influenza vaccine antigen-containing aqueous solution that contains an influenza vaccine antigen, a disaccharide, and an amino acid, wherein the amino acid is at least one selected from the group consisting of arginine, lysine, proline, threonine, ornithine, alanine, cysteine, phenylalanine, glycine; hydroxyproline, and salts of these.

The present invention is specifically described in the following.

The dried influenza vaccine preparation of the present invention contains an influenza vaccine antigen.

The "dried preparation" as used herein refers to a preparation having a moisture content of 15% by mass or less. Among the dried preparations, those having a moisture content of 10% by mass or less are particularly referred to as low-moisture-content dried preparations.

The "moisture content" as used herein is determined in accordance with the Japanese Pharmacopoeia Sixteenth Edition, General test, Loss on Drying Test (hereafter, also simply referred to as a loss on drying test). In other words, the moisture content is determined from the mass reduction rate of a sample of the dried influenza vaccine preparation of the present invention after heating at 105° C. for three hours.

The dried influenza vaccine preparation of the present invention is preferably a solid preparation. The solid preparation as used herein refers to a drug preparation that is solid, namely has no fluidity, at room temperature (25° C.).

The strain of influenza virus used in the influenza vaccine antigen is not particularly limited. Examples include an influenza A vaccine antigen and an influenza B vaccine antigen. Only one strain of influenza virus may be used for the influenza vaccine antigen. Preferably, the influenza vaccine contains two or more types of influenza vaccine antigens including one or more influenza A vaccine antigens and one or more influenza B vaccine antigens. In particular, among the influenza A vaccine antigens, preferred are H1N1 antigen and H3N2 antigen. Among the influenza B vaccine antigens, preferred are Yamagata lineage and Victoria lineage, and also Brisbane lineage.

The influenza vaccine is not particularly limited, and may contain a live virus or an inactivated antigen. In particular, the influenza virus antigen is preferably an inactivated antigen. The inactivated antigen may be an inactivated whole virus, a split vaccine antigen, or a subunit vaccine antigen, preferably a split vaccine antigen or a subunit vaccine antigen, more preferably a split vaccine antigen.

The inactivated antigen is preferably a split vaccine antigen or subunit vaccine antigen prepared in the following manner: growing virus particles in embryonated eggs; disrupting the virus particles with an organic solvent or a surfactant; and isolating or purifying viral proteins depending on the type. The inactivated antigen is more preferably a split vaccine antigen.

The type of the split vaccine antigen is not particularly limited. Examples include hemagglutinin (HA) antigen, neuraminidase (NA) antigen, matrix (M1) antigen, matrix (M2) antigen, and nucleoprotein (NP)) antigen. Among these, preferred is hemagglutinin (HA) antigen that is a virus surface antigen in view of inducing immunity that is effective for infection control by administration of the dried influenza vaccine preparation.

The influenza vaccine antigen may contain two or more vaccine antigens or a single vaccine antigen.

A method for producing the influenza vaccine antigen is not particularly limited, and any conventionally known method may be employed. For example, the influenza vaccine antigen may be produced from a virus stock solution that is prepared by infecting chicken eggs, cells, or the like by a usual method with virus strains isolated from patients with influenza or animals infected with influenza and culturing the virus strains, followed by purification. Alternatively, the influenza vaccine antigen may be produced from a genetically engineered recombinant virus or specific antigen produced in various cells.

The amount of the influenza vaccine antigen contained in the dried influenza vaccine preparation of the present invention is only required to be at least an effective amount. For example, the total amount of the antigen(s) contained in the dried influenza vaccine preparation of the present invention is preferably within a range of 0.01 µg to 1.0 mg per dose. If the amount is less than 0.01 µg, the infection control or the function as a therapeutic agent may be insufficient. If the amount is more than 1.0 mg, a safety problem may arise. The lower limit of the amount of the antigen is more preferably 0.1 µg and the upper limit thereof is more preferably 500 µg.

The "mass of the antigen" as used herein refers to the total mass of all the antigen proteins contained in the antigen in the vaccine composition, unless otherwise specified. Accordingly, in the case where the antigen is a substance derived from a living body such as viruses, the mass of the antigen refers to the mass of all the proteins contained in the antigen. In the case where plural antigens are contained, the total mass thereof is meant.

The dried influenza vaccine preparation of the present invention contains a disaccharide and an amino acid.

Since the dried influenza vaccine preparation of the present invention contains such components, the activity of the influenza vaccine antigen can be maintained high even if the preparation is stored without strict temperature control.

The disaccharide is preferably at least one selected from the group consisting of trehalose, isomalt, sucrose, maltose, melibiose, palatinose, and lactulose. Any of these disaccharides can stabilize the influenza vaccine antigen and is contained in the dried influenza vaccine preparation of the present invention.

The disaccharide is more preferably at least one selected from the group consisting of trehalose, isomalt, and sucrose.

The disaccharide is still more preferably trehalose and/or isomalt. The trehalose and isomalt which are non-reducing saccharides are preferred because they especially exhibit a high stabilizing effect and can prevent Maillard reaction, which may occur as a side reaction in the case where saccharide is formed into a dried preparation together with an amino acid.

The amount of the disaccharide is preferably 5 to 70% by mass, more preferably 20 to 70% by mass based on the total mass of the dried influenza vaccine preparation.

If the amount of the disaccharide is less than 5% by mass, the vaccine may not be sufficiently stabilized.

The amino acid is preferably at least one selected from the group consisting of arginine, lysine, proline, threonine, ornithine, alanine, cysteine, phenylalanine, glycine, hydroxyproline, and salts of these. Any of these amino acids stabilizes the influenza vaccine and is contained in the dried influenza vaccine preparation of the present invention.

The amino acid is more preferably an L-amino acid.

The amino acid is still more preferably at least one selected from the group consisting of arginine hydrochloride, proline, threonine, and ornithine hydrochloride because the activity of the influenza vaccine antigen can be stably maintained high even if the preparation is stored without strict temperature control.

Moreover, the amino acid is most preferably arginine hydrochloride. In the case where the arginine hydrochloride is used together with a disaccharide, the activities of type A influenza antigens, in particular H3N2 antigen, and type B influenza antigens can be more effectively stably maintained. Thus, the activities of all of H1N1 antigen, H3N2 antigen, and type B influenza antigens can be stably maintained.

The salt as used herein refers to any organic acid salt or inorganic acid salt. Preferred is a pharmaceutically acceptable salt. In particular, more preferred is hydrochloride.

The amount of the amino acid is preferably 0.1 to 50% by mass, more preferably 1 to 40% by mass, most preferably 1 to 10% by mass, based on the total mass of the dried influenza vaccine preparation. If the amount of the amino acid is less than 0.1% by mass, sufficient vaccine stability may not be achieved.

The dried influenza vaccine preparation of the present invention preferably contains an immunostimulant (adjuvant).

The adjuvant may be at least one selected from the group consisting of a toll-like receptor 4 (TLR4) agonist, a toll-like receptor 2/6 (TLR2/6) agonist, and a cyclic dinucleotide or a derivative or salt thereof. Preferred among these is a TLR4 agonist.

The TLR4 agonist is preferably a lipopolysaccharide or a salt thereof. The lipopolysaccharide as used herein may be, as well as the lipopolysaccharide itself, a derivative or a variant thereof as long as it keeps the properties of the lipopolysaccharide.

The lipopolysaccharide may be an extract from a gram negative bacterial cell wall or a variant thereof, and may also be a synthetic lipopolysaccharide.

Examples of the gram negative bacterium include bacteria of genus *Acetobacter*, genus *Achromobacter*, genus *Acidicaldus*, genus *Acidiphilium*, genus *Acidisphaera*, genus *Acidocella*, genus *Acidomonas*, genus *Agrobacterium*, genus *Asaia*, genus *Bacillus*, genus *Belnapia*, genus *Brucella*, genus *Bacteroides*, genus *Bordetella*, genus *Clostridium*, genus *Craurococcus*, genus *Chiamydia*, genus *Enterobacter*, genus *Escherichia*, genus *Flavohacterium*, genus *Francisella*, genus *Gluconacetobacter*, genus *Gluconobacter*, genus *Haemophilus*, genus *Kozakia*, genus *Klebsiella*, genus *Leahibacter*, genus *Leciercia*, genus *Legionella*, genus *Methanoculleus*, genus *Methanosarcina*, genus *Micrococcus*, genus *Murlcoccus*, genus *Neisserla*, genus *Necasaia*, genus *Oleomonas*, genus *Pantoea*, genus *Plesiomonas*, genus *Paracraurococcus*, genus *Pseudomonas*, genus *Prophyromonas*, genus *Proteus*, genus *Rahnella*, genus *Rhodopila*, genus *Roseococcus*, genus *Rubritepida*, genus *Salmonella*, genus *Shigella*, genus *Stenortophomonas*, genus *Saccharibacter*, genus *Serratia*, genus *Stella*, genus *Swaminathania*, genus *Vibrio*, genus *Vparahaemolyticus*, genus *Teichococcus*, genus *Xanthomonas*, genus *Yersinia*, genus *Zymomonas*, and genus *Zavarzinia*. Preferred examples of the gram negative bacteria include bacteria of genus *Eschericha*, genus *Shigella*, genus *Salmonella*, genus *Klebsiella*, genus *Proteus*, genus *Yersinia*, genus *Vibrio*, genus *Vparahaemolyticus*, genus *Haemophilus*, genus *Pseudomonas*, genus *Legionella*, genus *Bordetella*, genus *Brucella*, genus *Francisella*, genus *Bacteroides*, genus *Neisseria*, genus *Chlamydia*, genus *Plesiomonas*, genus *Prophyromonas*, genus *Pantoea*, genus *Agrobacterium*, genus *Stenortophomonas*, genus *Enterobacter*, genus *Acetobacter*, genus *Xanthomonas*, and genus *Zymomonas*.

In particular, an extract or variant obtained from bacteria of genus *Escherichia*, genus *Salmonella*, genus *Pantoea*, genus *Acetobacter*, genus *Zymomonas*, genus *Xanthomonas*, or genus *Enterobacter* is preferred. They are contained in many kinds of food and herbal medicines used from ancient times and therefore are guaranteed to be safe to living bodies. In particular, an extract or variant obtained from bacteria of genus *Pantoea* is now used as health food and is considered to be more effective. These extracts or variants derived from bacteria can be used as they are.

In the case where the extract obtained from a gram negative bacterial cell wall or a purified lipopolysaccharide is used as the lipopolysaccharide, the safety thereof to living bodies commonly needs to be considered. Variants obtained by detoxifying these may also be used. In contrast, bacteria of genus *Acetobacter* (e.g., *Acetobacter aceti, Acetobacter xylinum, Acetobacter orientalis*), genus *Zymomonas* (e.g., *Zymomonas mobilis*), genus *Xanthomonas* (e.g., *Xanthomonas campestris*), genus *Enterobacter* (e.g., *Enterobacter cloacae*), and genus *Pantoea* (e.g., *Pantoea agglomerans*) are contained in many kinds of food and herbal medicines used from ancient times and therefore are guaranteed to be safe to living bodies. Accordingly, extracts derived from these bacteria or a purified lipopolysaccharide can be used as they are.

Examples of the derivatives of the lipopolysaccharide include derivatives obtained by removing the polysaccharide moiety of the lipopolysaccharide, specifically, Lipid A, monophosphoryl lipid A, and 3-deacylated monophosphoryl lipid A (3D-MPL).

The Lipid A obtained by removing the polysaccharide moiety of the lipopolysaccharide may be an isolate derived from the gram negative bacterium or one synthesized to have the same structure as that of the isolate derived from the gram negative bacterium.

As a variant of the Lipid A, a dephosphorylated monophosphoryl lipid or a salt or derivative thereof may also be suitably used. The derivative of a monophosphoryl lipid as used herein may be used in the present invention as long as it keeps properties as the monophosphoryl lipid. In particular, from the standpoint of safety to living bodies, 3D-MPL having a record as an immunostimulant for medical applications or a non-deacylated synthetic qlucopyranosyl lipid as disclosed in US 2010/0310602 A is preferred.

The monophosphoryl lipid used may also be suitably one derived from *Salmonella* which is safe and has been used precedertly.

The cyclic dinucleotide is preferably a cyclic dipurine nucleotide, and may also be a salt or derivative thereof as long as it keeps properties of a cyclic dipurine nucleotide. As the cyclic dipurine nucleotide, for example, c-di-GMP that is a cyclic diguanosine monophosphate or c-di-AMP that is a cyclic diadenosine monophosphate is preferably used in terms of the safety.

The amount of the adjuvant in the dried influenza vaccine preparation of the present invention is preferably within a range of 0.1 µg to 100 mg per dose for each individual. If the amount is less than 0.1 µg, the infection control or the function as a therapeutic agent may be insufficient if the amount is more than 100 mg, a safety problem may arise. The lower limit of the amount of the immunostimulant is more preferably 0.3 µg and the upper limit thereof is more preferably 50 mg.

The activity of the influenza vaccine antigen in the dried influenza vaccine preparation of the present invention can be stably maintained high even if the preparation is stored without strict temperature control, and thus the preparation can be easily distributed and stored, compared to conventional liquid preparations.

The activity of the influenza vaccine antigen in the dried influenza vaccine preparation of the present invention can be stably maintained high even if the preparation is stored, for example, at a storage temperature of 0° C. to 50° C. The lower limit of the storage temperature is more preferably 2° C. and the upper limit thereof is more preferably 40° C.

The present invention also relates to a method for producing a dried influenza vaccine preparation including: drying an influenza vaccine antigen-containing aqueous solution that contains an influenza vaccine antigen, a disaccharide, and an amino acid, wherein the disaccharide is at least one selected from the group consisting of trehalose and sucrose, and the amino acid is at least one selected from the group consisting of arginine, lysine, proline, threonine, ornithine, alanine, cysteine, phenylalanine, glycine, hydroxyproline, and salts of these. The method is useful because the influenza vaccine antigen contained in the dried preparation can exhibit its activity without an activity decrease during the production process of the dried influenza vaccine preparation.

The total amount of the influenza vaccine antigen(s) in the influenza vaccine antigen-containing aqueous solution is preferably 0.01 µgHA/mL or more. If the total amount is less than 0.01 µgHA/mL, the effectiveness of the dried influenza vaccine preparation may be lowered. The lower limit of the total amount is more preferably 0.1 µgHA/mL.

The total amount of the influenza vaccine antigen in the influenza vaccine antigen-containing aqueous solution is preferably 20 mgHA/mL or less from the standpoint of the stability of the antigen. The upper limit of the amount is more preferably 10 mgHA/mL.

The amount of the disaccharide in the influenza vaccine antigen-containing aqueous solution is preferably 0.1 to 20% by mass, more preferably 0.5 to 15% by mass.

If the amount of the disaccharide is less than 0.1% by mass, the stability of the influenza vaccine antigen in the dried influenza vaccine preparation may be insufficient. If the amount of the disaccharide is more than 20% by mass, the viscosity of the influenza vaccine antigen-containing solution may be very high to cause troubles in the production. In addition, the hygroscopicity of the dried influenza vaccine preparation increases, possibly lowering the activity of the influenza antigen if the preparation is stored without strict temperature control.

The amount of the amino acid in the influenza vaccine antigen-containing aqueous solution is preferably 0.01 to 25% m/v. If the amount is less than 0.01% m/v, the stabilizing effect due to the amino acid may be insufficient. If the amount is more than 25% m/v, the dried influenza vaccine preparation will have high hygroscopicity, and the activity of the influenza vaccine antigen may decrease if the preparation is stored without strict temperature control. In addition, crystallization of the amino acid may be promoted, decreasing the activity of the influenza vaccine antigen. The upper limit of the amount is more preferably 20% m/v. The lower limit is more preferably 0.05% m/v and the upper limit is still more preferably 15% m/v.

The influenza vaccine antigen is preferably dried under non-thermal conditions because it is thermally unstable.

The method of drying under non-thermal conditions is not particularly limited. Yet, it is preferably a reduced-pressure drying method or a lyophilization method, with the lyophilization method being particularly preferred. The lyophilization method is not particularly limited. Any method that uses a conventionally known lyophilization device can be used.

The dried influenza vaccine preparation of the present invention may be used as a tablet or particulate preparation obtained by drying the influenza vaccine antigen-containing aqueous solution by lyophilization, or as a film preparation obtained by reduced-pressure drying the influenza vaccine antigen-containing aqueous solution. Alternatively it may be used as a tablet obtained by drying the influenza vaccine antigen-containing aqueous solution, followed by mixing and tableting.

Advantageous Effects of Invention

The activity of the influenza vaccine antigen in the dried influenza vaccine preparation of the present invention can be stably maintained high even if the preparation is stored without strict temperature control, and thus the preparation can be easily distributed and stored, compared to conventional liquid preparations.

In addition, the dried influenza vaccine preparation of the present invention is prepared in such a manner that the influenza vaccine antigen is stabilized by a disaccharide and an amino acid which can be stably supplied at low cost. Thus, the dried influenza vaccine preparation of the present invention can also be stably supplied.

Further, the dried influenza vaccine preparation of the present invention can be used as it is or by being dissolved or dispersed in a solvent that can be administered to a living body (such as a normal saline solution or water for injection) when used. Thus, the preparation can be used in various administration forms. Specifically, the preparation can be used as an injectable drug or a mucosal administration preparation to be administered to nasal mucous membrane, intraoral mucous membrane (e.g., buccal side, under the tongue, on the tongue, back of the tongue), ocular mucous membrane, ear mucous membrane, genital mucous membrane, pharynx mucous membrane, respiratory tract mucous membrane, bronchial mucous membrane, pulmonary mucous membrane, gastric mucous membrane, intestinal mucous membrane, or rectal mucous membrane.

Moreover, administration of the dried influenza vaccine preparation of the present invention in a dosage form allowing administration to intraoral mucous membrane contributes to excellent compliance based on the following factors. Specifically, noninvasive administration is allowed; patients are free from pain or fear of injections; patients can perform administration by themselves as the administration is easy; medical professionals can avoid a risk of infection due to needle pricking; in the case where repetitive administration is needed, the ambulatory frequency can be reduced to contribute to the improvement in quality of life of the patient; and medical wastes (e.g., needles) which necessitate special disposition are not generated. In addition, administration of the dried influenza vaccine preparation of the present invention in a dosage form allowing administration to a mucous membrane can induce higher immunity (IgA antibody) compared to injections.

DESCRIPTION OF EMBODIMENTS

The present invention is described in more detail below with reference to, but not limited to, examples.

EXAMPLES 1 to 40

(Lyophilized Influenza HA Vaccine Preparation)
Trehalose (Hayashibara Co., Ltd.) or sucrose (Wako Pure Chemical Industries, Ltd.) as a disaccharide and L(+)-arginine hydrochloride (Wako Pure Chemical Industries, Ltd.), L-lysine hydrochloride (Wako Pure Chemical Industries, Ltd.), L(-)-proline (Wako Pure Chemical Industries, Ltd.), L-threonine (Wako Pure Chemical Industries, Ltd.), or L(+)-arginine (Wako Pure Chemical Industries, Ltd.) as an amino acid as shown in Tables 1 to 4 were added to influenza HA antigen (A(H1N1): A/California/7/2009, A(H3N2): A/Victoria/361/2011, B/Yamagata lineage: B/Wisconsin/1/2010, and B/Victoria lineage: B/Brisbane/60/2008, all produced by the Research. Foundation for Microbial Diseases of Osaka University), and then PBS for adjustment having the composition described below (phosphate-buffered sodium chloride solution) was added to the mixture to prepare an influenza vaccine antigen-containing aqueous solution containing 10% m/v of the disaccharide, 5% m/v of the amino acid, and 100 µgHA/mL of the influenza HA antigen (1000 parts by mass of the disaccharide and 500 parts by mass of the amino acid per part by mass of influenza HA antigen). The thus-obtained influenza vaccine antigen-containing aqueous solution (30 µL) was dispensed in a 1.5-mL safe-lock tube (Eppendorf) and lyophilized. Thus, a dried influenza vaccine preparation was obtained.
PBS for Adjustment
Sodium chloride (Wako Pure Chemical Industries, Ltd.): 4.25 g
Disodium hydrogen phosphate 12-hydrate (Wako Pure Chemical Industries, Ltd.): 1.76 g
Sodium dihydrogen phosphate 2-hydrate (Wako Pure Chemical Industries, Ltd.): 0.35 g
Distilled water filled up to 500 mL in a measuring flask Comparative Examples 1, 15, 29, and 43

(Saccharide- and Amino Acid-Free Influenza HA Vaccine Preparation)
A dried influenza vaccine preparation was obtained in the same manner as in Example 1 except that no disaccharide or amino acid was added as shown in Tables 1 to 4.

Comparative Examples 2 to 4, 16 to 18, 30 to 32, and 44 to 46

(Saccharide-Added Influenza HA Vaccine Preparation)
A dried influenza vaccine preparation was obtained in the same manner as in Example 1 except that trehalose (Hayashibara Co., Ltd.), sucrose (Wako Pure Chemical Industries, Ltd.), or glucose (Wake Pure Chemical Industries, Ltd.) was added as a saccharide as shown in Table 1 to 4 to produce a preparation containing 20% m/v of the saccharide and 100 µgHA/mL of the influenza HA antigen (50 parts by mass of the saccharide per part by mass of the influenza HA antigen), and no amino acid was added.

Comparative Examples 5 to 9, 19 to 23, 33 to 37, and 47 to 51

(Amino Acid-Added Influenza HA Vaccine Preparation)
A dried influenza vaccine preparation was obtained in the same manner as in Example 1 except that L (+)-arginine hydrochloride (Wako Pure Chemical industries, Ltd.), L-lysine hydrochloride (Wako Pure Chemical industries, Ltd.), L(-)-proline (Wako Pure Chemical industries, Ltd.), L-threonine (Wako Pure Chemical Industries, Ltd.), or L(+)-arginine (Wako Pure Chemical Industries, Ltd.) was added as an amino acid as shown in Tables a to 4 to produce a preparation containing 10% m/v of the amino acid and 100 µgHA/mL of the influenza HA antigen (100 parts by mass of the amino acid per part by mass of the influenza HA antigen), and no saccharide was added.

Comparative Examples 10 to 14, 24 to 20, 38 to 42, and 52 to 56

(Glucose-Added Influenza HA Vaccine Preparation)
A dried influenza vaccine preparation was obtained in the same manner as in Example 1 except that glucose (Wako Pure Chemical Industries, Ltd.) was added as a saccharide.
<Measurement Example: Measurement of the Activity of Influenza HA Vaccine Antigen: Single Radial Immunodiffusion Method (SKID Method)
Agarose (AMRESCO) was added to the PBS for adjustment to a concentration of 1% by mass, and heated to be completely dissolved. After a temperature decrease to about 60° C., an appropriate amount of an antiserum corresponding to the influenza HA vaccine was added and stirred. The mixture was poured into a heat-resistant vessel (10 cm in diameter), and cooled at room temperature to be solidified. Using a dedicated punch, 4×4 pieces of holes (4 mm in diameter) were made in the obtained solid, thereby preparing a gel for SRID analysis.
Each of the dried influenza vaccine preparations according to the examples and comparative examples was dissolved in the PBS for adjustment and then diluted to a desired concentration. A surfactant was further added to a final concentration of 1% and completely dissolved therein Thus obtained solution was used as a sample solution.
As the standard solution, a 30 µg/mL solution of the influenza HA antigen was prepared using an influenza vaccine stock solution. At that time, additives contained in the sample solution (compounding agents and surfactants used in the preparation) were each added to the vaccine stock solution to the same final concentration as that of the sample solution, and appropriately diluted with the PBS for adjustment to be completely dissolved. Similarly, a 22.5 µg/mL solution, a 15 µg/mL solution, and a 7.5 µg/mL solution of the influenza HA antigen were prepared.
The standard solutions at four concentrations and the sample solution were each applied to the SRID gel in an amount of 10 µL/well, and allowed to react under the wet condition at 25° C. for 18 to 24 hours.
The SRID gel taken out from the vessel was sandwiched between two sheets of filter paper, then further sandwiched between two sheets of paper having high absorbability, and dehydrated under a weight. The dehydrated gel was further subjected to air drying to be completely dried. The resulting gel was dyed in a coomassie brilliant blue (BIO-RAD) staining solution for an appropriate time, transferred to a destaining solution, and destained until an appropriate chromatic figure was obtained. Then, the SRID gel was spread on a GelBond Film (LONZA) and completely dried. The area of the obtained precipitate ring was measured using Image J software.

A calibration curve was created based on the concentrations and the areas of the obtained precipitate rings of the standard solutions, and the area of the precipitate ring of the sample solution was measured. Based on the calibration curve, the HA titer was calculated. Tables 6 to 9 show the obtained HA titer as a relative value (%) assuming that the titer of an influenza HA vaccine-added placebo solution was 100%.

TABLE 1

|  | Influenza HA antigen | Saccharide | Amino acid | Measurement of activity (%) | | |
|---|---|---|---|---|---|---|
|  |  |  |  | Immediately after preparation | Two weeks later | One month later |
| Comparative Example 1 | A/California/7/2009 (A(H1N1)) |  | Not added | 25.4 | 23.0 | 23.9 |
| Comparative Example 2 |  | Trehalose | — | 84.1 | 93.4 | 81.9 |
| Comparative Example 3 |  | Sucrose | — | 90.8 | 85.7 | 86.4 |
| Comparative Example 4 |  | Glucose | — | 54.9 | 50.4 | 49.1 |
| Comparative Example 5 |  | — | L(+)-arginine hydrochloride | 74.2 | 93.8 | 77.8 |
| Comparative Example 6 |  | — | L-lysine hydrochloride | 83.2 | 78.9 | 74.4 |
| Comparative Example 7 |  | — | L-threonine | 72.8 | 80.2 | 77.5 |
| Comparative Example 8 |  | — | L(−)-proline | 76.3 | 73.0 | 71.8 |
| Comparative Example 9 |  | — | L(+)-arginine | 55.9 | 56.1 | 51.5 |
| Example 1 |  | Trehalose | L(+)-arginine hydrochloride | 99.0 | 102.8 | 100.4 |
| Example 2 |  |  | L-lysine hydrochloride | 100.3 | 101.9 | 98.7 |
| Example 3 |  |  | L-threonine | 102.2 | 98.1 | 99.1 |
| Example 4 |  |  | L(−)-proline | 99.5 | 97.0 | 100.7 |
| Example 5 |  |  | L(+)-arginine | 80.3 | 83.9 | 79.9 |
| Example 6 |  | Sucrose | L(+)-arginine hydrochloride | 101.8 | 99.1 | 102.9 |
| Example 7 |  |  | L-lysine hydrochloride | 101.4 | 102.5 | 99.7 |
| Example 8 |  |  | L-threonine | 98.1 | 97.2 | 101.9 |
| Example 9 |  |  | L(−)-proline | 97.7 | 98.9 | 102.4 |
| Example 10 |  |  | L(+)-arginine | 78.4 | 75.9 | 80.3 |
| Comparative Example 10 |  | Glucose | L(+)-arginine hydrochloride | 83.3 | 81.4 | 79.6 |
| Comparative Example 11 |  |  | L-lysine hydrochloride | 74.8 | 77.2 | 78.2 |
| Comparative Example 12 |  |  | L-threonine | 82.1 | 83.1 | 79.4 |
| Comparative Example 13 |  |  | L(−)-proline | 82.1 | 81.8 | 80.6 |
| Comparative Example 14 |  |  | L(+)-arginine | 70.7 | 65.9 | 67.4 |

TABLE 2

|  | Influenza HA antigen | Saccharide | Amino acid | Measurement of activity (%) | | |
|---|---|---|---|---|---|---|
|  |  |  |  | Immediately after preparation | Two weeks later | One month later |
| Comparative Example 15 | A/Victoria/361/2011 (A(H3N2)) |  | Not added | 30.3 | 35.0 | 29.8 |
| Comparative Example 16 |  | Trehalose | — | 97.5 | 73.2 | 71.0 |
| Comparative Example 17 |  | Sucrose | — | 81.4 | 77.0 | 74.7 |
| Comparative Example 18 |  | Glucose | — | 54.6 | 48.1 | 47.3 |
| Comparative Example 19 |  | — | L(+)-arginine hydrochloride | 88.1 | 79.3 | 89.6 |
| Comparative Example 20 |  | — | L-lysine hydrochloride | 75.9 | 85.4 | 81.9 |
| Comparative Example 21 |  | — | L-threonine | 71.8 | 77.3 | 78.2 |
| Comparative Example 22 |  | — | L(−)-proline | 80.7 | 73.5 | 72.1 |
| Comparative Example 23 |  | — | L(+)-arginine | 66.2 | 63.8 | 63.6 |
| Example 11 |  | Trehalose | L(+)-arginine hydrochloride | 99.4 | 97.1 | 103.0 |
| Example 12 |  |  | L-lysine hydrochloride | 99.8 | 100.1 | 100.7 |
| Example 13 |  |  | L-threonine | 102.4 | 97.8 | 99.7 |
| Example 14 |  |  | L(−)-proline | 100.3 | 98.9 | 101.6 |
| Example 15 |  |  | L(+)-arginine | 64.4 | 69.3 | 69.5 |
| Example 16 |  | Sucrose | L(+)-argnine hydrochloride | 102.4 | 101.2 | 100.9 |
| Example 17 |  |  | L-lysine hydrochloride | 101.1 | 99.8 | 100.4 |
| Example 18 |  |  | L-threonine | 98.6 | 102.5 | 101.2 |
| Example 19 |  |  | L(−)-proline | 101.9 | 100.3 | 98.9 |
| Example 20 |  |  | L(+)-arginine | 70.9 | 62.1 | 61.7 |
| Comparative Example 24 |  | Glucose | L(+)-arginine hydrochloride | 61.4 | 62.2 | 64.7 |
| Comparative Example 25 |  |  | L-lysine hydrochloride | 63.9 | 61.5 | 62.4 |
| Comparative Example 26 |  |  | L-threonine | 65.7 | 70.6 | 69.0 |
| Comparative Example 27 |  |  | L(−)-proline | 60.3 | 63.9 | 59.8 |
| Comparative Example 28 |  |  | L(+)-arginine | 57.3 | 50.6 | 53.6 |

TABLE 3

| | Influenza HA antigen | Saccharide | Amino acid | Measurement of activity (%) | | |
|---|---|---|---|---|---|---|
| | | | | Immediately after preparation | Two weeks later | One month later |
| Comparative Example 29 | B/Wisconsin/1/2010 | | Not added | 37.7 | 34.0 | 31.1 |
| Comparative Example 30 | (B/Yamagata lineage) | Trehalose | — | 102.2 | 86.8 | 81.8 |
| Comparative Example 31 | | Sucrose | — | 101.8 | 99.8 | 97.3 |
| Comparative Example 32 | | Glucose | — | 64.6 | 59.5 | 58.3 |
| Comparative Example 33 | | — | L(+)-arginine hydrochloride | 93.9 | 80.9 | 84.6 |
| Comparative Example 34 | | — | L-lysine hydrochloride | 88.7 | 83.1 | 79.5 |
| Comparative Example 35 | | — | L-threonine | 90.1 | 86.9 | 86.0 |
| Comparative Example 36 | | — | L(−)-proline | 94.5 | 89.1 | 80.4 |
| Comparative Example 37 | | — | L(+)-arginine | 71.2 | 65.5 | 63.7 |
| Example 21 | | Trehalose | L(+)-arginine hydrochloride | 101.2 | 100.4 | 103.4 |
| Example 22 | | | L-lysine hydrochloride | 101.8 | 99.3 | 98.7 |
| Example 23 | | | L-threonine | 98.1 | 97.8 | 95.9 |
| Example 24 | | | L(−)-proline | 100.1 | 98.3 | 97.6 |
| Example 25 | | | L(+)-arginine | 73.8 | 69.9 | 65.5 |
| Example 26 | | Sucrose | L(+)-arginine hydrochloride | 99.9 | 98.8 | 101.3 |
| Example 27 | | | L-lysine hydrochloride | 100.5 | 98.4 | 97.8 |
| Example 28 | | | L-threonine | 102.4 | 101.7 | 99.6 |
| Example 29 | | | L(−)-proline | 96.4 | 95.9 | 95.4 |
| Example 30 | | | L(+)-arginine | 61.9 | 59.9 | 57.2 |
| Comparative Example 38 | | Glucose | L(+)-arginine hydrochloride | 65.8 | 60.3 | 53.1 |
| Comparative Example 39 | | | L-lysine hydrochloride | 70.5 | 69.2 | 55.7 |
| Comparative Example 40 | | | L-threonine | 68.0 | 62.2 | 61.9 |
| Comparative Example 41 | | | L(−)-proline | 64.4 | 60.1 | 59.0 |
| Comparative Example 42 | | | L(−)-arginine | 60.3 | 58.9 | 52.6 |

TABLE 4

| | Influenza HA antigen | Saccharide | Amino acid | Measurement of activity (%) | | |
|---|---|---|---|---|---|---|
| | | | | Immediately after preparation | Two weeks later | One month later |
| Comparative Example 43 | B/Brisbane/60/2008 | | Not added | 38.7 | 51.7 | 51.1 |
| Comparative Example 44 | (B/Victoria lineage) | Trehalose | — | 102.6 | 83.6 | 91.8 |
| Comparative Example 45 | | Sucrose | — | 95.8 | 94.4 | 93.8 |
| Comparative Example 46 | | Glucose | — | 61.4 | 59.0 | 57.6 |
| Comparative Example 47 | | — | L(+)-arginine hydrochloride | 95.0 | 96.0 | 94.5 |
| Comparative Example 48 | | — | L-lysine hydrochloride | 93.6 | 91.2 | 90.5 |
| Comparative Example 49 | | — | L- threonine | 89.9 | 86.5 | 85.9 |
| Comparative Example 50 | | — | L(−)-proline | 92.2 | 88.7 | 85.3 |
| Comparative Example 51 | | — | L(+)-arginine | 69.1 | 65.5 | 63.1 |
| Example 31 | | Trehalose | L(+)-arginine hydrochloride | 98.9 | 100.6 | 102.0 |
| Example 32 | | | L-lysine hydrochloride | 101.6 | 101.1 | 99.5 |
| Example 33 | | | L-threonine | 102.8 | 99.4 | 99.1 |
| Example 34 | | | L(−)-proline | 100.4 | 97.3 | 95.8 |
| Example 35 | | | L(+)-arginine | 75.4 | 70.8 | 69.0 |
| Example 36 | | Sucrose | L(+)-arginine hydrochloride | 101.9 | 100.4 | 98.8 |
| Example 37 | | | L-lysine hydrochloride | 97.5 | 97.2 | 95.6 |
| Example 38 | | | L-threonine | 100.7 | 97.4 | 96.8 |
| Example 39 | | | L(−)-proline | 98.2 | 98.0 | 94.2 |
| Example 40 | | | L(+)-arginine | 70.2 | 68.9 | 66.1 |
| Comparative Example 52 | | Glucose | L(+)-arginine hydrochloride | 72.3 | 68.5 | 68.4 |
| Comparative Example 53 | | | L-lysine hydrochloride | 75.8 | 70.2 | 69.7 |
| Comparative Example 54 | | | L-threonine | 73.3 | 72.8 | 71.2 |
| Comparative Example 55 | | | L(−)-proline | 71.6 | 69.0 | 67.3 |
| Comparative Example 56 | | | L(+)-arginine | 68.6 | 64.6 | 58.4 |

As shown in Tables 1 to 4, in the examples in which a disaccharide and an amino acid were added, the activities of all the influenza HA vaccine antigens could be stably maintained.

In particular, in the examples in which arginine hydrochloride, lysine hydrochloride, threonine, or preline was used as an amino acid, the activities of the influenza HA vaccine antigens were stably maintained high. In particular, Examples 1, 6, 11, 16, 21, 26, 31, and 36 show that in the case where arginine hydrochloride and a disaccharide are used together, the activities of the influenza HA vaccine antigens including all of A(H1N1), A(H3N2), B/Yamagata lineage, and B/victoria lineage are stably maintained extremely high.

In Comparative Examples 2 to 4, 16 to 18, 30 to 32, and 44 to 46 in which only a saccharide was added, Comparative Examples 5 to 9, 19 to 23, 33 to 37, and 47 to 51 in which only an amino acid was added, and in Comparative Examples 1, 15, 29, and 43 in which both a saccharide and an amino acid were not added, the activities of the influenza HA vaccine antigens were not stabilized in comparison with those of the examples.

In Comparative Examples 10 to 14, 24 to 28, 38 to 42, and 52 to 56 in which glucose was contained as a saccharide, the activities of the influenza HA vaccine antigens were not stabilized in comparison with those of the examples in which trehalose or sucrose was contained.

The moisture contents measured by the loss on drying test of the dried influenza vaccine preparations of the examples and comparative examples were all 10% by mass or less.

The present invention can provide a dried influenza vaccine preparation in which the activity of an influenza vaccine antigen can be stably maintained high even if the preparation is stored without strict temperature control and which can be stably supplied. The present invention can also provide a method for producing the dried influenza vaccine preparation.

The invention claimed is:

1. A dried influenza vaccine preparation comprising:
   an influenza vaccine antigen;
   a disaccharide selected from the group consisting of trehalose, isomalt, sucrose, maltose, melibiose, palatinose, and lactulose; and
   an amino acid selected from the group consisting of arginine hydrochloride, lysine, proline, threonine, ornithine, cysteine, hydroxyproline, and salts of these.

2. The dried influenza vaccine preparation according to claim 1, wherein the influenza virus antigen is an inactivated antigen.

3. The dried influenza vaccine preparation according to claim 2, wherein the inactivated antigen is a split vaccine antigen or a subunit vaccine antigen.

4. The dried influenza vaccine preparation according to claim 2, wherein the inactivated antigen is a split vaccine antigen.

5. A method for producing a dried influenza vaccine preparation comprising:
   drying an influenza vaccine antigen-containing aqueous solution that contains an influenza vaccine antigen, a disaccharide selected from the group consisting of trehalose, isomalt, sucrose, maltose, melibiose, palatinose, and lactulose, and an amino acid, wherein the amino acid is at least one selected from the group consisting of arginine hydrochloride, lysine, proline, threonine, ornithine, cysteine, hydroxyproline, and salts of these.

* * * * *